United States Patent [19]

Ambrose

[11] 3,965,724

[45] June 29, 1976

[54] DEVICE AND METHOD FOR CALCULATING TEMPERATURE AND WATER VAPOR PRESSURE

[76] Inventor: Wallace R. Ambrose, 39 Melba St., Downer, Australian Capital Territory 2602, Australia

[22] Filed: Dec. 6, 1974

[21] Appl. No.: 530,292

[52] U.S. Cl. ............................. 73/64.2; 55/270; 55/387; 55/522; 73/339 R
[51] Int. Cl.² ..................... G01N 5/02; G01K 3/04
[58] Field of Search ............... 73/64.2, 76, 339 R, 73/73, 28; 55/18, 21, 275, 274, 158, 387–389, 270, 522

[56] References Cited
UNITED STATES PATENTS

| | | | |
|---|---|---|---|
| 1,601,308 | 9/1926 | Hill | 55/274 |
| 1,698,320 | 1/1929 | Sharp | 55/388 X |
| 2,105,683 | 1/1938 | Burdick | 73/73 |
| 2,196,021 | 4/1940 | Merrill | 55/388 |
| 2,283,867 | 5/1942 | Flosdorf et al. | 55/275 X |
| 2,552,477 | 5/1951 | Cole | 73/339 X |
| 2,792,706 | 5/1957 | Mauret | 73/76 |
| 3,055,206 | 9/1962 | Watson et al. | 73/76 X |
| 3,142,830 | 7/1964 | Patrick et al. | 55/275 X |
| 3,235,089 | 2/1966 | Burroughs | 55/389 X |
| 3,256,675 | 6/1966 | Robb | 55/158 X |
| 3,463,000 | 8/1969 | Broadwin | 73/76 |

*Primary Examiner*—Herbert Goldstein
*Assistant Examiner*—Frederick Shoon

[57] ABSTRACT

A device and method for determining the time-temperature history of a solid, liquid or gaseous medium where the temperature is expressed as a single value of the total temperature conditions to which the medium has been subjected over a given time, the invention involving use of a fluid tight container having a spherical cell of constant wall thickness and permeable to water vapor, the cell containing a dry desiccant and the container being filled with water. Similarly, the vapor pressure history of the medium may be determined by use of a second, non-containerized, spherical cell together with the containerized cell.

11 Claims, 4 Drawing Figures

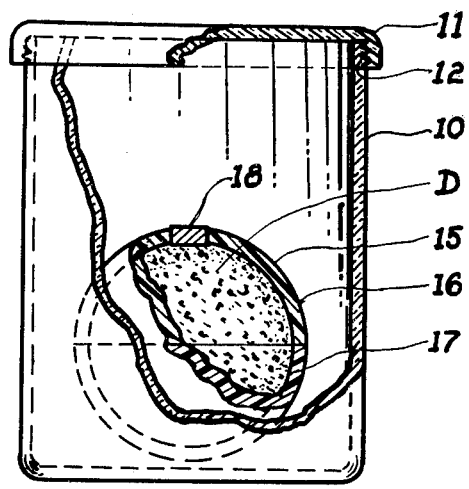
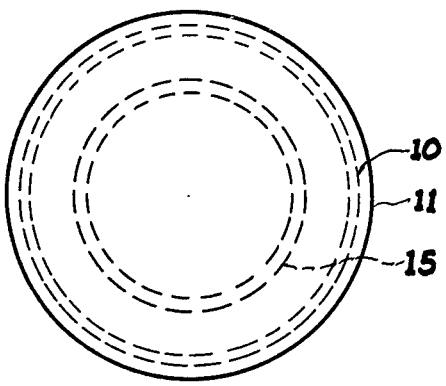
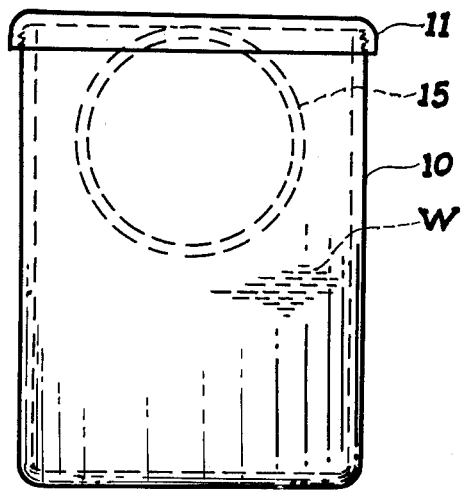

DEVICE AND METHOD FOR CALCULATING TEMPERATURE AND WATER VAPOUR PRESSURE

FIELD OF THE INVENTION

This invention relates to a device and a method for determining the temperature of a medium where the temperature is expressed as a single value of the total temperature conditions to which the medium has been subjected over a given time. The medium concerned may be solid, liquid or gaseous, for example, soil, water, including sea water, or air. The invention may also be used in water vapour pressure determinations.

BACKGROUND OF THE PRIOR ART

A known procedure for determining the temperature of a medium, such as soil, over a chosen period of time is to read and record individual temperatures at more or less regular intervals over the chosen time and then to calculate the arithmetic mean of the recorded temperatures. The readings may be made directly from thermometers or thermocouples placed in the medium. The accuracy of the calculated mean is related to the number of recordings made, the amplitude and frequency of the natural temperature variation and the amount of disturbance caused to the natural temperature regime by the device employed and/or by the act of making the reading. The devices employed are also generally in an exposed position and consequently open to interference by animals. Since many readings and recordings are usually necessary, labour and administrative costs are high and the overall operation is expensive. Further, quite often the sites at which the devices are placed are in remote areas which causes additional labour charges and other difficulties in obtaining regular readings.

It is an object of this invention to provide a cumulative record of a medium's temperature history over a period of time without the requirement for making numerous measurements over a period.

It is a further object to reduce the disturbance to the medium during the period.

A still further object is to effect the temperature recording at a diminished cost.

SUMMARY OF THE INVENTION

This invention provides a device for use in determining the temperature of a medium as a single value of the total temperature conditions to which the medium has been subjected over a selected period of time, such device comprising a fluid tight container the interior of said container containing a hollow spherical cell of constant wall thickness, and permeable to water vapour, said cell containing a dry desiccant material in particulate form and said container being filled to capacity with water.

The invention also provides a method for use in determining the temperature of a medium as a single value of the total temperature conditions to which the medium has been subjected over a selected period of time, such method comprising the steps of weighing the sphere mentioned above before it is placed in its fluid tight container containing water, at the end of the selected period of time, removing the sphere, carefully drying the outside of the sphere, weighing the sphere, calculating the weight increase of the sphere, comparing the weight increase with a standard scale (determined in a manner hereinafter described) and thus estimating the temperature of the medium as a single value of the total temperature conditions to which the medium has been subjected over the selected time:

The manner of determining the standard scale is to take $n$ (with $n < 30$) identical spheres $x_1, x_2 \ldots x_n$ containing the same weight of dry desiccant and to place them in $n$ fluid tight containers filled with water, each container being held at $n$ different temperatures $T_1, T_2 \ldots T_n$ respectively for a time of one year. At the end of the year, the $n$ spheres are removed from their containers and the outside of each carefully dried. The weight increase of each sphere is then calculated and denoted as $W_1, W_2 \ldots W_n$. The weight increases $W_1, W_2 \ldots W_n$ are graphed against their respective temperatures $T_1, T_2 \ldots T_n$ and a smooth curve drawn through the points $(w_1, T_1), (w_2, T_2) \ldots (w_n, T_n)$, thus determining the standard scale.

In the accompanying sheet of drawings forming a part of this specification, one illustrative embodiment of the invention has been shown.

In these drawings:

FIG. 1 is a side elevational view of a device for use in determining the temperature of a medium, the device being shown partially in section;

FIG. 2 is a top plan view of the device; and

FIG. 3 is a side elevational view of the container filled with water and having a sphere floating therein, FIG. 4 a side elevational view partially in section of an embodiment of this invention useful in measuring the vapor pressure history of a medium.

DESCRIPTION OF PREFERRED EMBODIMENTS

Figure 4:
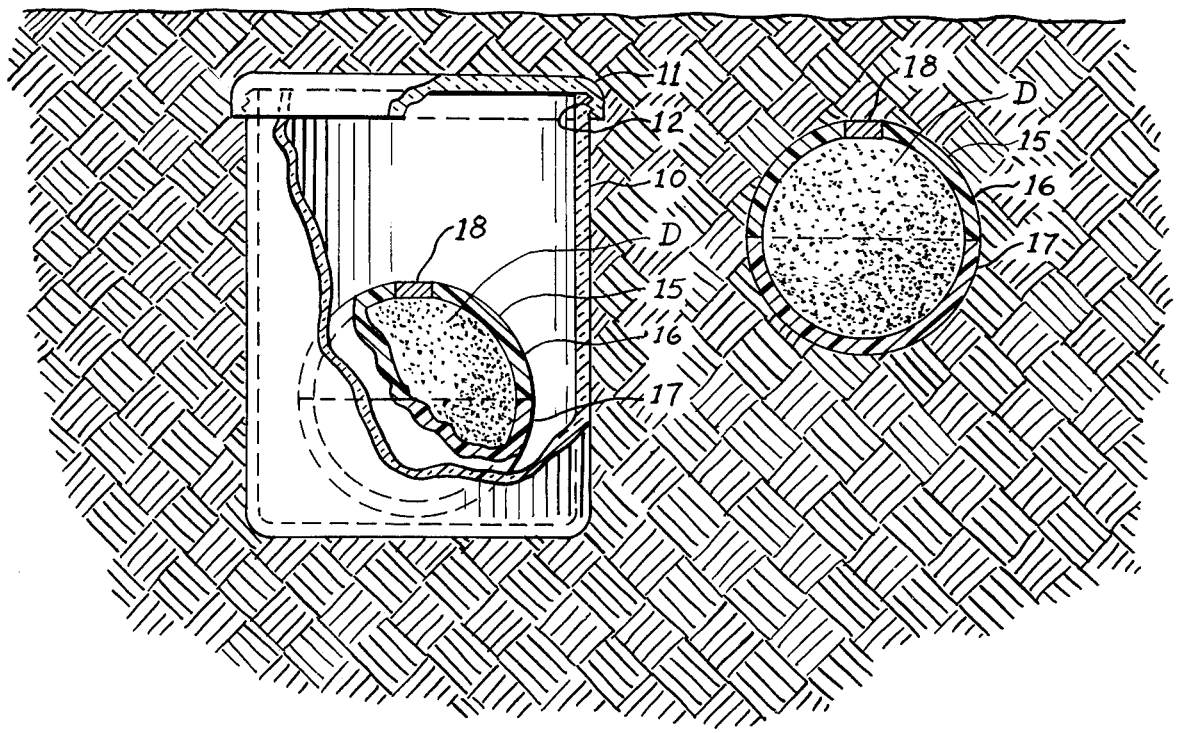

The fluid tight container is preferably a glass container 10 fitted with a lid 11 having internal threads 12 to seal against entry or exit of air or liquid. The size is not of critical importance, but necessarily the container must have an opening sufficiently large to allow the sphere to be placed in it and also to be removed. A typical shape is a cylinder about 5 cm. high and 3.5 cm. in diameter with a wall thickness of about 2 to 3 mm.

The hollow spherical cell 15 containing the desiccant material D is desirably about 15 mm. to 50 mm. in diameter, preferably about 27 mm. and has a wall thickness within the range of about 0.25 mm. to about 5 mm., desirably 1.0mm. As mentioned before the wall thickness for each spherical cell 15 must be constant and the material from which the cell 15 is made must be permeable to water vapour.

A particularly desirable material is a thermoplastic material which beside being permeable to water vapour has also an extremely high impact strength, a resistance to water absorption and can easily be solvent welded. A polycarbonate marketed by General Electric Corporation and identified as "Lexan 141R clear" has been found to be an excellent material of construction. The material has a specific gravity of about 1.2, a Rockwell hardness of m 78 and a water absorption in 24 hours of about 1.5% (A.S.T.M.). A general description of the production and properties of polycarbonates is given in a book by William S. Christopher and Daniel W. Fox, 1962 ed., Reinhold Publishing Co., New York, entitled "Polycarbonates".

Epoxy resins have been used successfully. Some other materials pose problems e.g. nylon absorbs moisture and other materials tend to suffer degradation in the form of delamination after a period of one year even in cold water.

The spheres 15 may be made in a manner known per se. In respect of polycarbonate spheres the following brief description is given:

A. Tooling - Tooling required is a three cavity Injection Mould fully hardened and polished to produce one top half 16 of the cell 15, one bottom half 17 and one sealing plug 18.

B. Manufacture - Manufacture consists of moulding the three articles and solvent welding the top and bottom half together.

The spheres 15 are then filled and plugged. The solvent used to weld the parts is dichloro methane. Manufacturing tolerances of the spheres for a 27 mm. diameter, 1 mm. wall thickness are ±.05mm. diameter and ± .01 mm. wall thickness.

A preferred desiccant D is activated zeolite 4A which is a so termed molecular sieve. A description of this zeolite and other suitable zeolites is given in the Third Edition. Second Impression (Revised) of "'Union Carbide' Molecular Sieves for Selective Absorption" by the B.D.H. Laboratory Chemicals Division. (Note the term 'Union Carbide' is a registered trademark of Union Carbide Corporation.)

When not in use the spheres 15 containing the dry desiccant D may be stored in the fluid tight containers 10 and surrounded by granules of a desiccant D.

In use, the spheres 15 together with the surrounding desiccant D are removed from the container 10. The sphere 15 is accurately weighed, replaced in the container 10 which is filled with water W and then sealed.

If it is desired to calculate the temperature of a medium such as soil in a particular site at a depth of one meter, for example, over a period of one year, the device is placed at that depth. At the expiry of the period of one year, the device is removed, the container 10 is opened, the water W and sphere 15 are removed from the soil, and the sphere 15 is carefully dried by a fine tissue and accurately weighed. If it is not practicable to weigh the sphere 15 at the site then the interior of the container 10 is dried, the sphere 15 replaced in it together with a desiccant D. The sphere 15 is then accurately weighed as soon as possible. By comparing the weight gain with the standard (determined as previously described), the temperature expressed as a single value of the total temperature conditions to which the soil has been subjected over the year in question is calculated by a direct graphical reading.

One use of the device and method of the invention is its application to obsidian hydration dating. Other uses include the application of the invention to agriculture and horticulture in determining temperature at various soil depths and the effect of varying temperatures on growth rates of plants and crops.

The determination of vapour pressure is an application of the main invention. It involves placing the device of the invention and also a non containerised hollow spherical cell of constant thickness containing a dry desiccant in close proximity in the medium as illustrated in FIG. 4. Depending on the nature of the medium it may be necessary to protect the cell by surrounding it (and also the device) by a fluid permeable cover - this could be e.g. metallic mesh box. The temperature of the medium is determined at the end of the chosen time as previously described; the weight increase of the non-enclosed hollow spherical cell is measured and by comparison with a standard the vapour pressure is calculated.

The method of establishing the standard is to maintain $n$ ($n \not< 30$) identical cells at a constant temperature T for a year in $n$ different vapour pressures $p_1, p_2 \text{---} p_n$. The weight increases are measured in the manner previously indicated (observing the same precautions) and indicated as $w_1, w_2 \text{---} w_n$ at each pressure $p_1, p_2 \text{---} p_n$ and the weight increase is graphed against pressure. A smooth curve is then drawn through the points ($w_1, p_1$), ($w_2, p_2$) ... ($w_n, p_n$). The same procedure is repeated for different temperatures T.

The vapour pressure thus obtained is the vapour pressure of the medium expressed as a single value of the total vapour pressure conditions to which the medium has been subjected over the chosen time.

It should be evident to, those skilled in the art that whilst the selected time for calibration of temperature and vapour pressure has been stated as one year, this could be varied and the standards calibrated for whatever period was desired e.g. 1 month, 6 months or 2 years. Further, whilst it has been described that the cells are spherical, this shape has been selected because it has the highest ratio of volume to surface area, other shapes regular or irregular could be used. However the results with spheres are more likely to be reproducible. Further the spheres are easy to manufacture, nevertheless, it is intended that the invention be not limited to spheres but include other shapes and to this extent it is intended that 'sphere' in the appended claims be given such a connotation.

Finally the invention has a useful application in oceanographic surveys where temperatures at varying depths may be calculated over lengthy periods.

What I claim is:

1. A device for use in determining the timetemperature history of a medium over a selected period of time, said device being in said medium at the time of measurement, such device comprising a fluid tight contaner, the interior of said container containing a hollow spherical cell of constant wall thickness, and permeable to water vapour, said cell containing a dry desiccant material in particulate form and said container being filled to capacity with water.

2. A device as claimed in claim 1, 2. A device as claimed in claim 1, in which the hollow spherical cell is composed of a polycarbonate.

3. A device as claimed in claim 1, in which the desiccant in the hollow spherical cell is a molecular sieve material.

4. A device as claimed in claim 3, in which the molecular sieve material is zeolite 4A.

5. A device for use in determining the timetemperature history of soil over a selected period of time, said device being used by being embedded in said soil, such device comprising a fluid tight container of cylindrical shape about 5cm. in height and about 3.5 cm. in diameter with a wall thickness of 2 to 3mm. containing a spherical cell composed of polycarbonate which is about 27mm. in external diameter and has a constant wall thickness of about 1mm., said cell being filled with zeolite 4A in particulate form and said container being filled to capacity with water.

6. A method for determining the time-temperature history of a medium over a selected period of time, using the device of claim 1, such method comprising the steps of weighing the spherical cell before it is placed in the fluid tight container containing water, placing the fluid tight container containing the cell into the medium to be measured, at the end of the selected period of time, removing the fluid tight container, removing the sphere therefrom drying the outside of the sphere, weighing the sphere, calculating the weight increase of the sphere, comparing the weight increase with the standard scale and thus estimating the time-temperature history of the medijm over the selected period of time.

7. A method for use in determining the time-temperature history of soil over a selected period of time comprising the step of weighing a spherical cell of constant wall thickness composed of polycarbonate and filled with a dry molecular sieve material, placing the sphere in a fluid tight container filled with water, sealing the container, putting the container in the soil at the desired depth, leaving the container in the soil until the selected period of time has expired, removing the container from the soil, recovering the spherical cell, weighing the spherical cell, calculating the increase in weight of the 8. A method as claimed in claim 7 in which the dry molecular sieve material is zeolite 4A.

9. A method as claimed in claim 8 in which the spherical cell has an external diameter of 27 mm. and a wall thickness of about 1 mm.

10. Apparatus for use in determining the vapour pressure history of a medium over a selected time which comprises a device as claimed in claim 1 placed in close proximity to a non-containerised hollow spherical cell containing a dry desiccant, both being situated in the medium.

11. A method for use in determining the vapour pressure history of a medium which comprises the steps of placing the apparatus of claim 10 in the medium, after having weighed the non-containerised cell, removing the apparatus at the end of the selected time, calculating the weight increase of the non-containerised cell, calculating the temperature-time history of the medium from the weight increase of the containerised cell, and then estimating the vapour pressure of the medium by reference to a standard scale.

* * * * *